United States Patent [19]

Becker et al.

[11] Patent Number: 5,728,170

[45] Date of Patent: Mar. 17, 1998

[54] BELOW-KNEE PROSTHESIS

[75] Inventors: Karl Becker; Manfred Krukenberg, both of Duderstadt, Germany

[73] Assignee: Otto Bock Orthopaedische Industrie Besitz- Und Verwaltungs-Kommanditgesellschaft, Duderstadt, Germany

[21] Appl. No.: 709,532

[22] Filed: Sep. 6, 1996

[30] Foreign Application Priority Data

Sep. 8, 1995 [EP] European Pat. Off. .............. 95114084

[51] Int. Cl.⁶ .................................................. A61F 2/80
[52] U.S. Cl. .................................... 623/37; 623/33
[58] Field of Search ................................. 623/32-37

[56] References Cited

U.S. PATENT DOCUMENTS

| | | |
|---|---|---|
| 1,868,303 | 7/1932 | Balch et al. . |
| 5,108,456 | 4/1992 | Coonan, III ................. 623/36 |
| 5,139,523 | 8/1992 | Paton et al. .................. 623/37 |
| 5,156,629 | 10/1992 | Shane et al. ................. 523/37 |
| 5,464,443 | 11/1995 | Wilson et al. ................. 623/37 |
| 5,549,709 | 8/1996 | Caspers ....................... 623/37 |

FOREIGN PATENT DOCUMENTS

| | | |
|---|---|---|
| 0 019 612 | 11/1980 | European Pat. Off. . |
| 2729800 | 1/1979 | Germany .................... 623/37 |
| 94 19 210.3 | 2/1995 | Germany . |
| 92/08425 | 5/1992 | WIPO . |
| 93/15696 | 8/1993 | WIPO . |
| 94/24965 | 11/1994 | WIPO . |

*Primary Examiner*—John G. Weiss
*Assistant Examiner*—Bruce E. Snow
*Attorney, Agent, or Firm*—Foley & Lardner

[57] ABSTRACT

A below-knee prosthesis with a rigid, bowl-shaped outer shaft having a closed distal end, and with a flexible inner shaft which is fitted therein in a removable manner and which likewise has a closed distal end and also an air chamber which can be inflated via a valve. To improve the wearing comfort a) the inner shaft is designed as a soft silicone shaft which can be rolled over the stump of the prosthesis user and which completely surrounds the stump and bears against it; b) the air chamber of the inner shaft completely surrounds the distal end of the stump and extends only over a small partial length of the inner shaft; c) a connector plug is secured on the distal end of the inner shaft and communicates with the air chamber via a through-bore to permit air exchange; d) an insertion opening adapted to the connector plug and receiving it in a detachable manner is provided in the distal end of the outer shaft; and e) a flexible tube is connected to the insertion opening, and its tube end guided to the outside is connected to an exhaust valve and a pump.

15 Claims, 5 Drawing Sheets

BELOW-KNEE PROSTHESIS

BACKGROUND OF THE INVENTION

The invention relates to a below-knee prosthesis with a rigid, bowl-shaped outer shaft having a closed distal end, and with a flexible inner shaft which is fitted therein in a removable manner and which likewise has a closed distal end and also an air chamber which can be inflated via a valve.

One known below-knee prosthesis is disclosed in U.S. Pat. No. 5,156,629, for example. The stump, provided with the inner shaft made of a polymer, is introduced from above into the hollow space of the outer shaft, this hollow space being open only at the top. The essential problem in terms of the wearing comfort arises from the change in volume of the stump. This change in volume is a result of the dynamic fluid volume in the body of the prosthesis user and can vary from one day to the next.

For this reason, the outer shaft and its hollow space must not be adapted unconditionally to the outer contour of the stump. Instead, a hollow space should be left to permit expansion of the stump, particularly in the area of the distal end of the stump. However, by doing this, the prosthesis user could well lose the prosthesis if the outer shaft becomes seemingly too large on account of atrophy or variation in volume of the stump. There is then a poor fit, in conjunction with an increased pumping action. Walking becomes awkward and is often accompanied by embarrassing noises and pain.

In the design described above, this problem is only partially resolved by inflating the inner shaft with air. Thus, in particular, there is no reliable frictional fit or positive fit between inner shaft and outer shaft.

SUMMARY OF THE INVENTION

The present invention is based on the object of improving the wearing comfort of the below-knee prosthesis which has been described above.

The below-knee prosthesis of the present invention achieves this object and other objects by means of the following features:

a) the inner shaft is designed as a soft silicone shaft which can be rolled over the stump of the prosthesis user and which completely surrounds the stump and bears against it;

b) the air chamber of the inner shaft completely surrounds the distal end of the stump and extends only over a small partial length of the inner shaft;

c) a connector plug is secured on the distal end of the inner shaft and communicates with the air chamber via a through-bore to permit air exchange;

d) an insertion opening adapted to the connector plug and receiving it in a detachable manner is provided in the distal end of the outer shaft; and e) a flexible tube is connected to the insertion opening, and its tube end guided to the outside is connected to an exhaust valve and a pump.

This solution permits, in the first instance, a controlled volume compensation between stump and outer shaft, and the fact that the forces acting on the stump are successfully distributed over a wide surface area increases the comfort and improves the mobility of the prosthesis user. The pressure which arises on pumping up the air chamber spreads into the soft-tissue parts, which are then additionally displaced around the bones and in this way increase the cushioning effect of the soft-tissue parts. The contact between stump and prosthesis is then optimal; it increases coordination (guidance of the prosthesis) and reduces trauma.

The air chamber according to the invention is an integral component of the inner shaft and lies snugly against the distal end of the stump around its complete circumference and in doing so adapts to any shape of stump. Because of the soft silicone, which is tolerated by the skin, no keratinization of the skin takes place; shearing forces are largely absorbed by the silicone. The inner shaft can therefore be worn directly on the skin. The grip (suspension) is obtained partly by frictional connection and partly by positive connection.

In order to prevent the inner shaft, and with it the stump, from being forced out of the outer shaft during the pumping-up of the air chamber, it is expedient to provide sufficient space for expansion in the outer shaft in the area of the distal end of the stump, over the height or length of the air chamber, in which case an at least partially and approximately cylindrical design of the hollow space of the outer shaft is expedient in the area lying above the expansion space. The difference in volume between stump and outer shaft can then be taken up completely by the air chamber. Total contact and final loading are achieved, and consequently an approximately ideal hydrostatic pressure within the stump.

One important aspect of the invention is, however, the additional securing of the inner shaft in the outer shaft by means of a frictional connection and positive connection of the distal end of the inner shaft, that is to say the distal end of the air chamber, with the distal end of the outer shaft. The plug connection provided in accordance with the invention provides a reliable connection between inner shaft and outer shaft as well as the unalterable position of the inner shaft in the outer shaft, and additionally affords the possibility of arranging the pump with the flexible tube for pumping up the air chamber directly in the outer shaft, separate from the inner shaft. Thus, the inner shaft no longer needs to have these components, with the result that it is possible to form a modular system by means of various silicone shafts. The stump of the patient is measured using modules varying in size, in order then to select, from the system of silicone inner shafts, one silicone shaft which is suitable in terms of its size.

The connection of the inner shaft to the outer shaft is effected automatically on introducing the stump already provided with the silicone shaft into the outer shaft. It is expedient in this respect if the connector plug is equipped along its length with rubber rings, to which annular locking slots are assigned in the insertion opening. By exchanging the rubber rings and/or by changing the number of rubber rings, the friction of the plug connection can be adjusted to the requirements of the patient. In addition, the air rings also serve to seal off the air system.

Further features of the invention are explained in greater detail below, together with further advantages of the invention, on the basis of an illustrative embodiment. Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

An embodiment serving as an example of the invention is represented in the drawings. The accompanying drawings, which are incorporated in and constitute a part of the specification, illustrate a presently preferred embodiment of the invention, and, together with the general description given above and the detailed description of the preferred embodiment given below, serve to explain the principles of the invention.

DETAILED DESCRIPTION OF THE PREFERRED EMBODIMENTS

Figure 1:
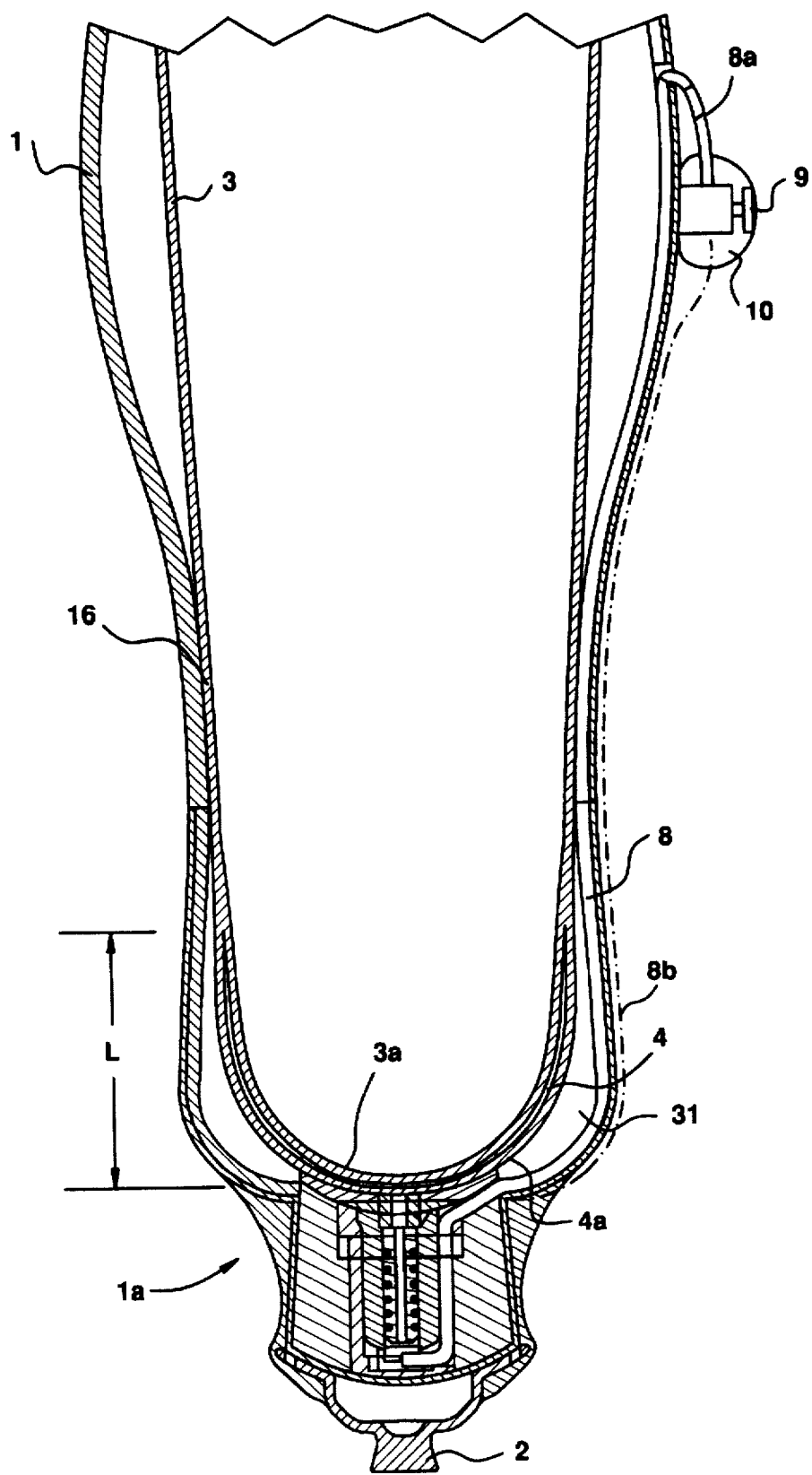
FIG. 1 shows a longitudinal section through a below-knee prosthesis according to the present invention.

The below-knee prosthesis represented in FIG. 1 has a rigid, bowl-shaped outer shaft 1 having a closed distal end 1a comprising an attachment 2 for a module and a flexible inner shaft 3 which is fitted therein in a removable manner and which likewise has a closed distal end 3a. This inner shaft 3 is designed as a soft silicone shaft which can be rolled over the stump of the prosthesis user and which completely surrounds the stump and bears against it. The silicone shaft is designed in two layers in its distal area and here forms a closed air chamber 4 which completely surrounds the distal end of the stump and extends only over a small partial length L of the inner shaft 3.

Figure 2:
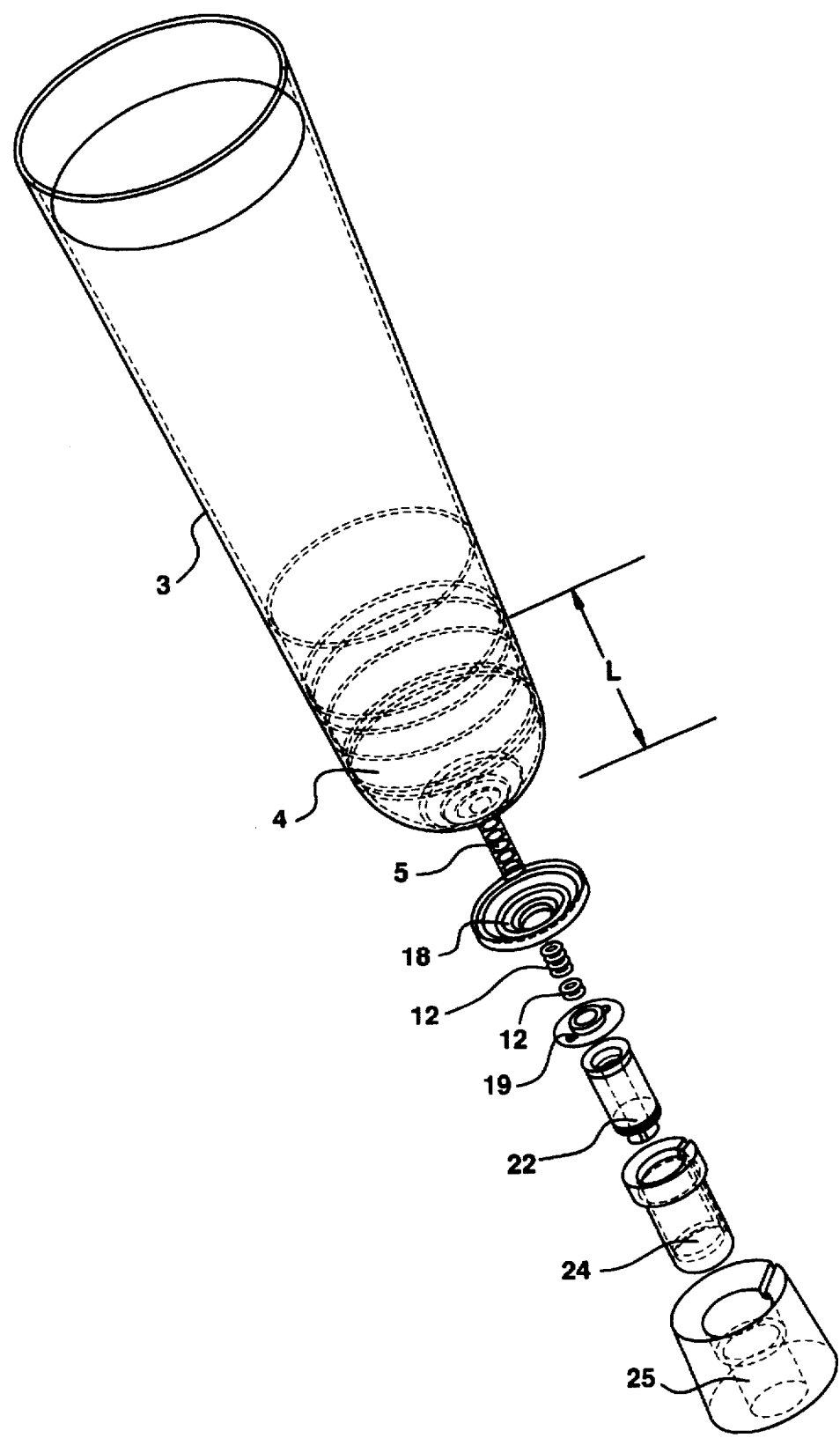
FIG. 2 shows an exploded view of the components of the below-knee prosthesis according to FIG. 1.

A connector plug 5 is secured on the distal end 3a of the inner shaft 3 (see FIGS. 2 and 3) and communicates with the air chamber 4 via a through-bore 6 to permit air exchange. An insertion opening 7 adapted to the connector plug 5 and receiving it in a detachable manner is provided in the distal end 1a of the outer shaft 1. A flexible tube 8 is connected to the insertion opening (see FIG. 1) and its tube end 8a guided to the outside is connected to an exhaust valve 9 and a pump 10. The tube end 8a is guided outward through the outer shaft 1; the exhaust valve 9 and the pump 10 are secured on the outside of the outer shaft 1. However, the flexible tube can be also be routed substantially outside the outer shaft 1 along the dot-and-dash line 8b.

Figure 3:
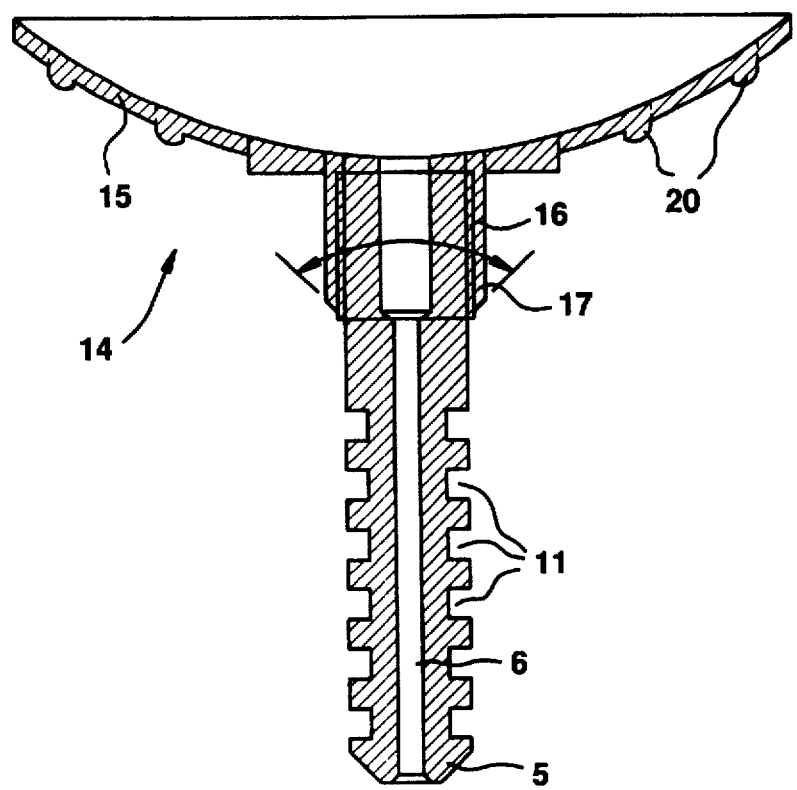
FIG. 3 shows, on an enlarged scale compared with FIG. 2, a longitudinal section through a plug-in part in accordance with the invention.

FIG. 3 shows that the connector plug 5 has six annular grooves 11 which are distributed along its length and which each serve to receive a rubber ring 12 (see FIG. 2) in an exchangeable manner. Annular locking slots 13 in the insertion opening 7 are assigned to these six rubber rings 12 which, in the inserted state, protrude somewhat beyond the circumferential surface of the connector plug 5.

Figure 4:
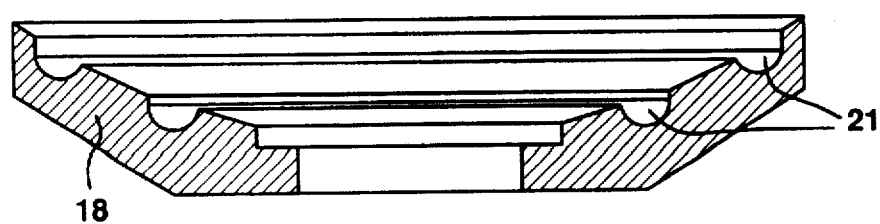
FIG. 4 shows a clamp piece in a sectional view in accordance with FIG. 3.

For securing the connector plug 5 on the distal end 3a of the inner shaft 3, a plug-in part 14 is provided which is arranged with a spherical-surface-shaped retainer plate 15 inside the air chamber 4, and whose distal wall 4a has passing through it a connection bushing 16 which is provided with an external thread 17. The connector plug 5, which is preferably made of aluminum, is pressed into the connection bushing 16, or else screwed in. A clamp piece 18 bearing from the outside against the distal end 3a of the inner shaft 3 is pushed onto the connection bushing 16 and can be tensioned in relation to the retainer plate 15 by means of an adjusting nut 19 which is screwed onto the connection bushing 16 (see FIG. 2). In order to ensure a non-slip fixing of the distal wall 4a of the air chamber 4, the retainer plate 15 has two annular beads 20 to which two annular grooves 21 in the clamp piece 18 are assigned (see FIG. 4).

Figure 5:
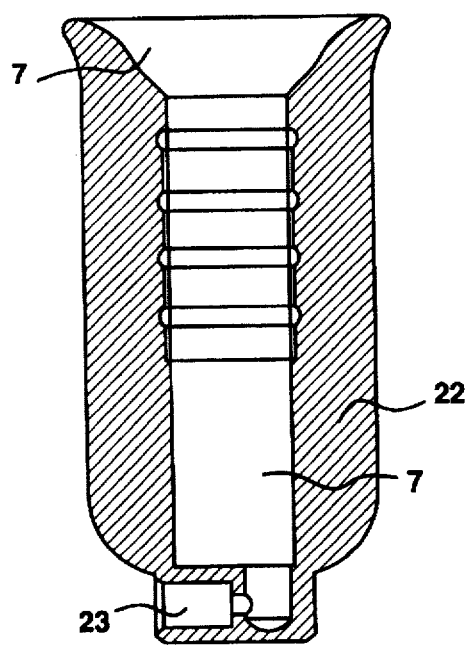
FIG. 5 shows a longitudinal section through a receiving piece of the present invention.
Figure 6:
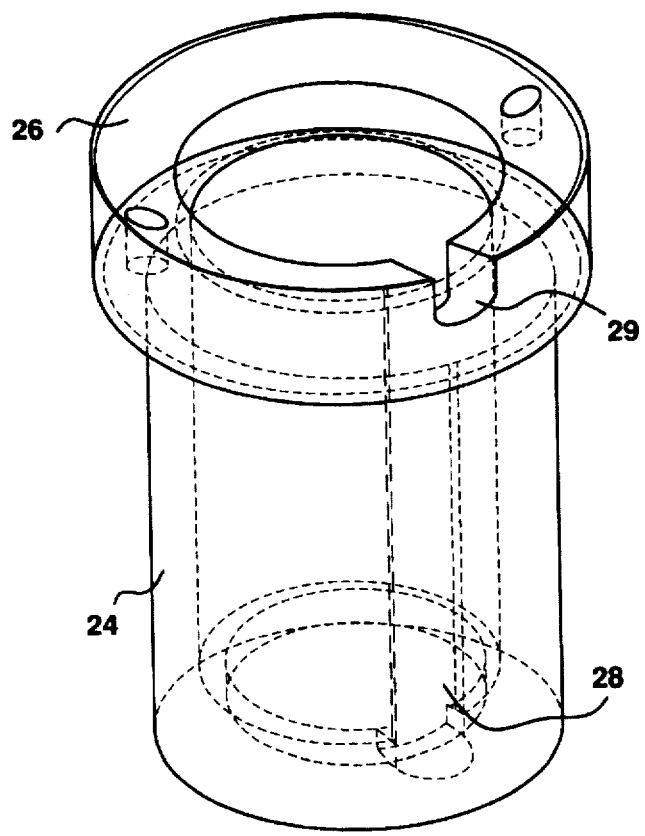
FIG. 6 shows a transitional receiving piece of the present invention in a perspective view.

The insertion opening 7 represents the central longitudinal bore of a receiving piece 22 (see FIG. 5) and communicates with a bore 23 which is provided in the distal end of the receiving piece and to which the flexible tube 8 is connected.

Figure 7:
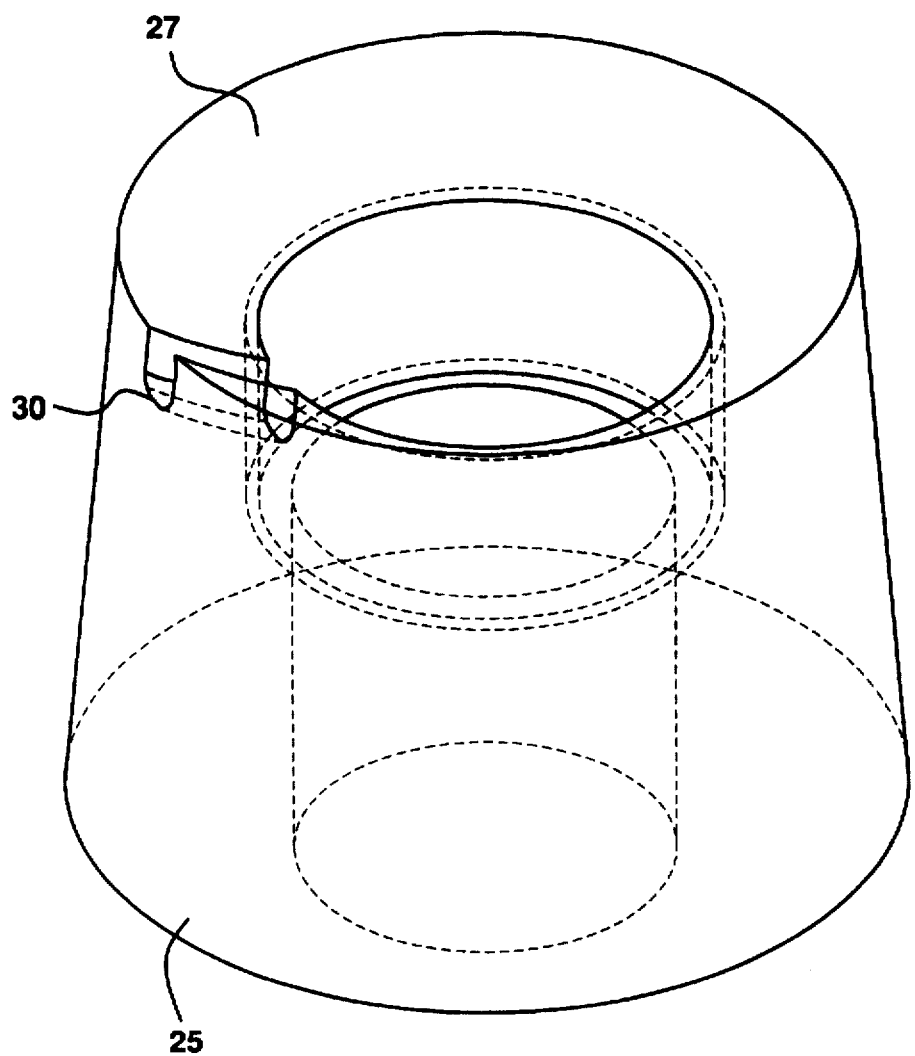
FIG. 7 shows an insert of the present invention in a perspective view.

The receiving piece 22 is surrounded by a pot-shaped transitional receiving piece 24 which is plugged into an insert 25 (see FIG. 7) which is laminated into the distal end 1a of the outer shaft 1. The transitional receiving piece 24 has an annular, cone-shaped or crown-shaped bearing surface 26 on which a rounded head of the adjusting nut 19 is supported. This bearing surface 26 lies flush with an annular face 27, surrounding it, of the insert 25.

For routing the flexible tube 8, the inner wall of the transitional receiving piece 24 is provided with an axially parallel groove 28 which is open toward the interior and which leads into a transverse groove 29 which is provided in the bearing surface 26 and which is flush with a correspondingly designed transverse groove 30 in the annular face 27 of the insert 25.

Retainer plate 15 with connection bushing 16, clamp piece 18, the adjusting nut 19 designed, for example, as a two-hole nut, receiving piece 22, transitional receiving piece 24 and insert 25 can be made of plastic.

The patient places the inner shaft 3 on the stump before stepping into the outer shaft 1 of the prosthesis and, by introducing the connector plug 5 into the insertion opening 7, effects an automatic locking and thus connection of the inner shaft 3 to the outer shaft 1. The friction can be adapted to the requirements of the patient by way of the rubber rings 12 of the connector plug 5. To achieve greater friction, rubber rings with a higher Shore hardness are chosen, with the result that a firmer frictional connection is provided. Conversely, to achieve a lower friction, a lower Shore hardness is chosen for the rubber rings, or else the number of rubber rings is reduced, as a result of which getting in and out is made easier for the patient. However, the rubber rings 12 at the same time serve as an air seal.

After getting the inner shaft 3 into the outer shaft 1, the patient himself can determine the volume in the distal section of the inner shaft 3 by pumping up the air chamber 4. The air connection is from the pump 10 via the flexible tube 8, the bore 23, the insertion opening 7 and the through-bore 6 in the connector plug 5.

If, when putting the prosthesis on, the connector plug 5 cannot from the outset be introduced fully into the insertion opening 7, the patient can exert a pressure in the distal direction on the plug connection by pumping up the air chamber 4, so that the friction of the rubber rings 12 in the receiving piece 22 is always utilized optimally, and the connector plug 5 equipped with the rubber rings 12 always has the same position in the receiving piece 22.

In order to prevent the inner shaft 3, and with it the stump, from being forced out of the outer shaft 1 during the pumping-up of the air chamber 4, a sufficient space for expansion 31 is provided in the outer shaft 1 in the area of the distal end of the stump, over the height or length L of the air chamber 4, which space 31 is adjoined at the top by an at least partially and approximately cylindrical section 1b of the outer shaft 1. In one preferred embodiment, the partial length L is about 7 cm.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A below-knee prosthesis comprising:
   a rigid outer shaft having a closed distal end; and
   a flexible inner shaft which is removably fitted in the outer shaft, the inner shaft having a closed distal end and an inflatable air chamber;
   wherein the inner shaft can be rolled over a stump of a prosthesis user and which is configured to completely surround the stump and bear against it;
   wherein the air chamber of the inner shaft is configured to completely surround the distal end of the stump and extends only over a small partial length of the inner shaft;
   wherein a connector plug is secured on the distal end of the inner shaft and communicates with the air chamber via a through-bore to permit air exchange;
   wherein the distal end of the outer shaft includes an insertion opening that receives the connector plug in a detachable manner for repeated removal and insertion of the inner shaft into the outer shaft; and
   wherein a flexible tube communicates with the insertion opening and an end of the tube, guided to the outside of the outer shaft, is connected to an exhaust valve and a pump to deflate and inflate the air chamber.

2. The below-knee prosthesis as claimed in claim 1, wherein the connector plug is equipped along its length with rubber rings corresponding to respective locking slots in the insertion opening.

3. The below-knee prosthesis as claimed in claim 2, wherein the rubber rings are arranged in an exchangeable manner.

4. The below-knee prosthesis as claimed in claim 3, wherein the connector plug is secured to the air chamber by a plug-in part, the plug in part including a spherical-surface-shaped retainer plate secured inside the air chamber, and a connection bushing passing through a distal wall of the air chamber for securing the connector plug.

5. The below-knee prosthesis as claimed in claim 2, wherein the connector plug is secured to the air chamber by a plug-in part, the plug in part including a spherical-surface-shaped retainer plate secured inside the air chamber, and a connection bushing passing through a distal wall of the air chamber for securing the connector plug.

6. The below-knee prosthesis as claimed in claim 1, wherein the connector plug is secured to the air chamber by a plug-in part, the plug-in part including a spherical-surface-shaped retainer plate secured inside the air chamber, and a connection bushing passing through a distal wall of the air chamber for securing the connector plug.

7. The below-knee prosthesis as claimed in claim 6, wherein the retainer plate or the clamp piece has at least one annular bead corresponding to an annular groove in the clamp piece or the retainer plate.

8. The below-knee prosthesis as claimed in claim 6, wherein a clamp piece is pushed onto the connection bushing provided with an external thread, which clamp piece bears from the outside against the distal end of the inner shaft and can be tensioned in relation to the retainer plate by an adjusting nut which is screwed onto the connection bushing.

9. The below-knee prosthesis as claimed in claim 8, wherein the retainer plate or the clamp piece has at least one annular bead corresponding to an annular groove in the clamp piece or the retainer plate.

10. The below-knee prosthesis as claimed in claim 8, wherein the transitional receiving piece has an annular, cone-shaped or crown-shaped bearing surface for engaging a rounded head of the adjusting nut.

11. The below-knee prosthesis as claimed in claim 1, wherein the insertion opening includes a central longitudinal bore in a receiving piece and communicates with a bore which is provided in the distal end of the receiving piece and to which the flexible tube is connected.

12. The below-knee prosthesis as claimed in claim 11, wherein the receiving piece is arranged inside a transitional receiving piece which is plugged into an insert which is fastened into the distal end of the outer shaft.

13. The below-knee prosthesis as claimed in claim 12, wherein the transitional receiving piece has an annular, cone-shaped or crown-shaped bearing surface for engaging a rounded head of the adjusting nut.

14. The below-knee prosthesis as claimed in claim 1, wherein the tube end is guided to the outside through the outer shaft, and the exhaust valve and the pump are secured on the outside of the outer shaft.

15. A below-knee prosthesis as claimed in claim 1, wherin the inner shaft is formed of soft silicone.

* * * * *